United States Patent
Govari et al.

(10) Patent No.: US 12,076,274 B2
(45) Date of Patent: Sep. 3, 2024

(54) ASPIRATION BYPASS CONTROL IN A PHACOEMULSIFICATION PROBE

(71) Applicant: JOHNSON & JOHNSON SURGICAL VISION, INC., Irvine, CA (US)

(72) Inventors: Assaf Govari, Haifa (IL); Yehuda Algawi, Binyamina (IL); Ilya Sitnitsky, Nahariya (IL); Eran Aharon, Haifa (IL); Stanislav Katzir, Hadera (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 1039 days.

(21) Appl. No.: 16/927,135

(22) Filed: Jul. 13, 2020

(65) Prior Publication Data

US 2022/0008251 A1 Jan. 13, 2022

(51) Int. Cl.
*A61F 9/007* (2006.01)
*A61M 39/22* (2006.01)
*A61M 39/00* (2006.01)

(52) U.S. Cl.
CPC ....... *A61F 9/00745* (2013.01); *A61M 39/223* (2013.01); *A61M 2039/0018* (2013.01); *A61M 2205/3331* (2013.01); *A61M 2205/50* (2013.01)

(58) Field of Classification Search
CPC .. A61F 9/00745; A61F 9/00736; A61F 9/007; A61M 2205/50; A61M 39/223; A61M 2205/3331; A61M 2039/0018; A61M 2205/3334; A61M 39/00;
(Continued)

(56) References Cited

U.S. PATENT DOCUMENTS

| 5,154,696 A | 10/1992 | Shearing |
| 6,605,054 B2 | 8/2003 | Rockley |
| 7,276,060 B2 | 10/2007 | Madden |

(Continued)

FOREIGN PATENT DOCUMENTS

| EP | 2164435 A1 | 3/2010 |
| EP | 2320842 | 6/2012 |
| WO | 2019068151 A1 | 4/2019 |

OTHER PUBLICATIONS

Dewang et al., Intraoperative Fracture of Phacoemulsification Tip, Middle East Afr J Ophthalmol. Jan.-Mar. 2014; 21(1):86-88.

*Primary Examiner* — Jason E Flick
(74) *Attorney, Agent, or Firm* — Johnson & Johnson Surgical Vision, Inc.

(57) ABSTRACT

A phacoemulsification system includes a phacoemulsification probe and a processor. The phacoemulsification probe includes (a) a needle configured for insertion into a lens capsule of an eye, and to be vibrated to emulsify a lens of the eye, (b) an irrigation channel for flowing irrigation fluid into the lens capsule, (c) an aspiration channel for removing material from the lens capsule, (d) a bypass channel fluidly coupled with the irrigation channel and with the aspiration channel, (e) a processor-controlled valve configured to control a level of fluid communication between the irrigation channel and the aspiration channel via the bypass channel, and (f) one or more sensors configured to measure fluid pressure at a distal portion of one or both of the irrigation channel and the aspiration channel. The processor is configured to adaptively adjust the valve based on the fluid pressure measured by the one or more sensors.

13 Claims, 4 Drawing Sheets

(58) Field of Classification Search
CPC .......... A61M 39/22; A61M 2039/0009; A61M 2205/33; A61M 2205/3344
See application file for complete search history.

(56) References Cited

U.S. PATENT DOCUMENTS

| | | |
|---|---|---|
| 8,241,242 B2 | 8/2012 | Sutton |
| 8,579,929 B2 | 11/2013 | Mackool et al. |
| 9,731,065 B2 | 8/2017 | Bourne et al. |
| 10,149,971 B2 * | 12/2018 | Liu ...................... A61M 39/22 |
| 2006/0224163 A1 | 10/2006 | Sutton |
| 2008/0058708 A1 | 3/2008 | Akahoshi |
| 2008/0294095 A1 | 11/2008 | Zacharias |
| 2013/0150782 A1 | 6/2013 | Sorensen et al. |
| 2014/0163455 A1 | 6/2014 | Wilson et al. |
| 2015/0157501 A1 | 6/2015 | Bourne et al. |
| 2015/0359666 A1 * | 12/2015 | Zacharias ............. A61M 1/842 604/151 |
| 2018/0028359 A1 * | 2/2018 | Gordon ................ A61M 1/732 |
| 2018/0055592 A1 | 3/2018 | Charles et al. |

\* cited by examiner

ASPIRATION BYPASS CONTROL IN A PHACOEMULSIFICATION PROBE

FIELD OF THE INVENTION

The present invention relates generally to phacoemulsification systems and probes, and particularly to aspiration bypass control.

BACKGROUND OF THE INVENTION

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution (BSS) to maintain the anterior chamber of the eye. After removing the cataract with phacoemulsification, the softer outer lens cortex is removed with suction. An intraocular lens (IOL) is then introduced into the empty lens capsule restoring the patient's vision.

Various techniques of irrigation and aspiration with a phacoemulsification probe were proposed in the patent literature. For example, U.S. Patent Application Publication 2019/068151 describes portable system and method that can be coupled with any commercially available phacoemulsification machine to provide a pressurized and stable flow of irrigating fluid to the eye during the surgery, thereby preventing some very undesirable complications. An automated air pump is used to push air into the fluid reservoir thus increasing the pressure with which the fluid flows into the eye. This increases the steady-state pressure of the eye making the anterior chamber deep and well maintained during the entire procedure, and makes phacoemulsification surgery a relatively safe procedure by reducing surge even at high vacuum levels.

As another example, U.S. Patent Application Publication 2015/0157501 describes an apparatus for insertion in an eye of a patient for aspirating material from the eye in the treatment of an ocular condition, the apparatus comprising a needle disposed at a distal end of the apparatus, an aspiration channel extending from a distal aperture of the needle to a proximal end of the apparatus, and an irrigation sleeve coaxially disposed about the needle. The aspiration channel comprises a proximal portion having a first diameter, a bypass portion having a second diameter and at least one bypass port, and a distal portion having a third diameter. The second diameter is larger than the first diameter. The irrigation sleeve and the needle form an annular irrigation passageway therebetween. The bypass port is shaped and configured to establish fluid communication between the irrigation passageway and the aspiration channel. In an embodiment, the user may control the vacuum pressure within the aspiration channel by selectively opening and closing the bypass port to selectively decrease and increase, respectively, the vacuum pressure while maintaining a substantially constant aspiration flow rate.

U.S. Patent Application Publication 2008/0294095 describes an outflow rate regulator system for use in a phacoemulsification system to prevent the anterior chamber collapses that occur after occlusion breaks caused by fluid surges in the aspiration line. The outflow rate regulator system consisting in a flow limiting device installed in the aspiration line capable of varying the section or the extension of a fluid passage as a function of the pressure difference across the outflow rate regulator access and exit sides. The device is designed to reduce the outflow fluid passage area as a function of an increasing pressure difference across the outflow rate regulator. Alternatively, the effective extension of a narrow fluid passage is designed to increase as the pressure difference across the outflow rate regulator increases. Resistance to flow is increased with increasing pressure differences across the device in reversible manner. Clogging of the narrow fluid passages is avoided by upstream removal of solid particles above a determined size by a retaining filter.

European Patent EP 2320842 describes a device for ophthalmic surgery, in particular for cataract removal, with intraocular pressure stabilization, comprising an irrigation line, within which an irrigation fluid flows, having an end portion capable to irrigate an eye, characterized in that it comprises at least one first source of irrigation fluid at a first pressure value connected through valve means to the end portion of the irrigation line, the valve means being controlled by control means on the basis of a pressure detection provided by pressure sensor means connected to the end portion of the irrigation line and capable to sense an intraocular pressure, whereby the control means opens the valve means when the pressure sensed by the sensor means is not higher than a second pressure value not higher than the first pressure value, thus putting the at least one first source in communication with the end portion of the irrigation line.

U.S. Pat. No. 8,241,242 describes a device for achieving high vacuum stability during phacoemulsification surgery, that includes a main aspiration line connected to a vacuum source which enables a fluid flow from a phacoemulsification handpiece tip to a drainage reservoir. A first tubing segment is provided in the main aspiration line along with a second tubing segment generally parallel to the first tubing section and a valve disposed in the second tubing segment regulates fluid flow through the second tubing segment in order to limit vacuum surge in the main aspiration line upon clearing of an occlusion in the phacoemulsification handpiece tip.

U.S. Pat. No. 6,605,054 describes phacoemulsification tip apparatus for a phacoemulsification/irrigation and aspiration handpiece having a drive assembly including a needle having a tip for emulsifying a cataracted lens and a lumen communication with primary and a secondary aspiration ports for aspirating emulsified lens. A sleeve establishes an annular passage around the needle and enables irrigation fluid to pass into an eye through a cornea/sclera wound while cooling the needle. A bypass port, disposed in said needle and under said compressible sleeve, establishes fluid communication between the lumen and the annular passage in order to enable irrigation fluid to pass into said lumen upon clogging of the primary and secondary aspiration ports, thus providing fluid surge protection. A depending member may be disposed within said compressible sleeve limits compression of opposing walls of said compressible sleeve in order to prevent contact of said compressible sleeve with the needle, maintain the annular passage flow of irrigation fluid past the needle and prevent the compressible sleeve from closing the bypass port.

SUMMARY OF THE INVENTION

An embodiment of the present invention that is described hereinafter provides a phacoemulsification system including a phacoemulsification probe and a processor. The phacoemulsification probe includes (a) a needle, which is configured to be inserted into a lens capsule of an eye and to be vibrated to emulsify a lens of the eye, (b) an irrigation channel for flowing irrigation fluid into the lens capsule, (c) an aspiration channel for removing material from the lens capsule, (d) a bypass channel fluidly coupled with the irrigation channel and with the aspiration channel, (e) a processor-controlled valve configured to control a level of fluid communication between the irrigation channel and the aspiration channel via the bypass channel, and (f) one or more sensors configured to measure fluid pressure at a distal portion of one or both of the irrigation channel and the aspiration channel. The processor is configured to adaptively adjust the valve based on the fluid pressure measured by the one or more sensors.

In some embodiments, the processor is configured to adjust the valve so as to maintain a vacuum level in the aspiration channel within a pre-specified limit.

In some embodiments, the processor is configured to adjust the valve so as to maintain a pressure level in the irrigation channel within a pre-specified limit.

In an embodiment, the one or more sensors include (i) a pressure sensor coupled to the distal portion of the irrigation channel, and (ii) a vacuum sensor coupled to the distal portion of the aspiration channel.

In some embodiments, the processor is configured to adjust the level of fluid communication by adjusting, using the valve, an opening of the bypass channel between the irrigation channel and the aspiration channel.

In an embodiment, the valve is a three-way rotatable valve. In another embodiment, the three-way rotatable valve is configured to simultaneously adjust an opening of the bypass channel while inversely adjusting the opening of the aspiration channel.

In some embodiments, the processor is included in the probe.

There is additionally provided, in accordance with another embodiment of the present invention, a method including inserting into an eye a phacoemulsification probe including a needle, an irrigation channel, an aspiration channel, a bypass channel, and a processor-controlled valve, wherein the bypass channel fluidly couples the irrigation channel to the aspiration channel, and wherein the valve is coupled with the bypass channel and the aspiration channel and is configured to control a level of fluid communication between the irrigation channel and the aspiration channel. The phacoemulsification needle is vibrated to emulsify a lens of the eye. Irrigation fluid is flowed via the irrigation channel into a lens capsule of the eye. Material from the lens capsule is removed via the aspiration channel. Using a processor, fluid pressure is measured at a distal portion of one or both of the irrigation channel and the aspiration channel, and the valve is adaptively adjusted based on the measured fluid pressure.

In some embodiments, adaptively adjusting the valve includes simultaneously adjusting an opening of the bypass channel while inversely adjusting the opening of the aspiration channel.

The present invention will be more fully understood from the following detailed description of the embodiments thereof, taken together with the drawings in which:

DETAILED DESCRIPTION OF EMBODIMENTS

Overview

Figure 1:
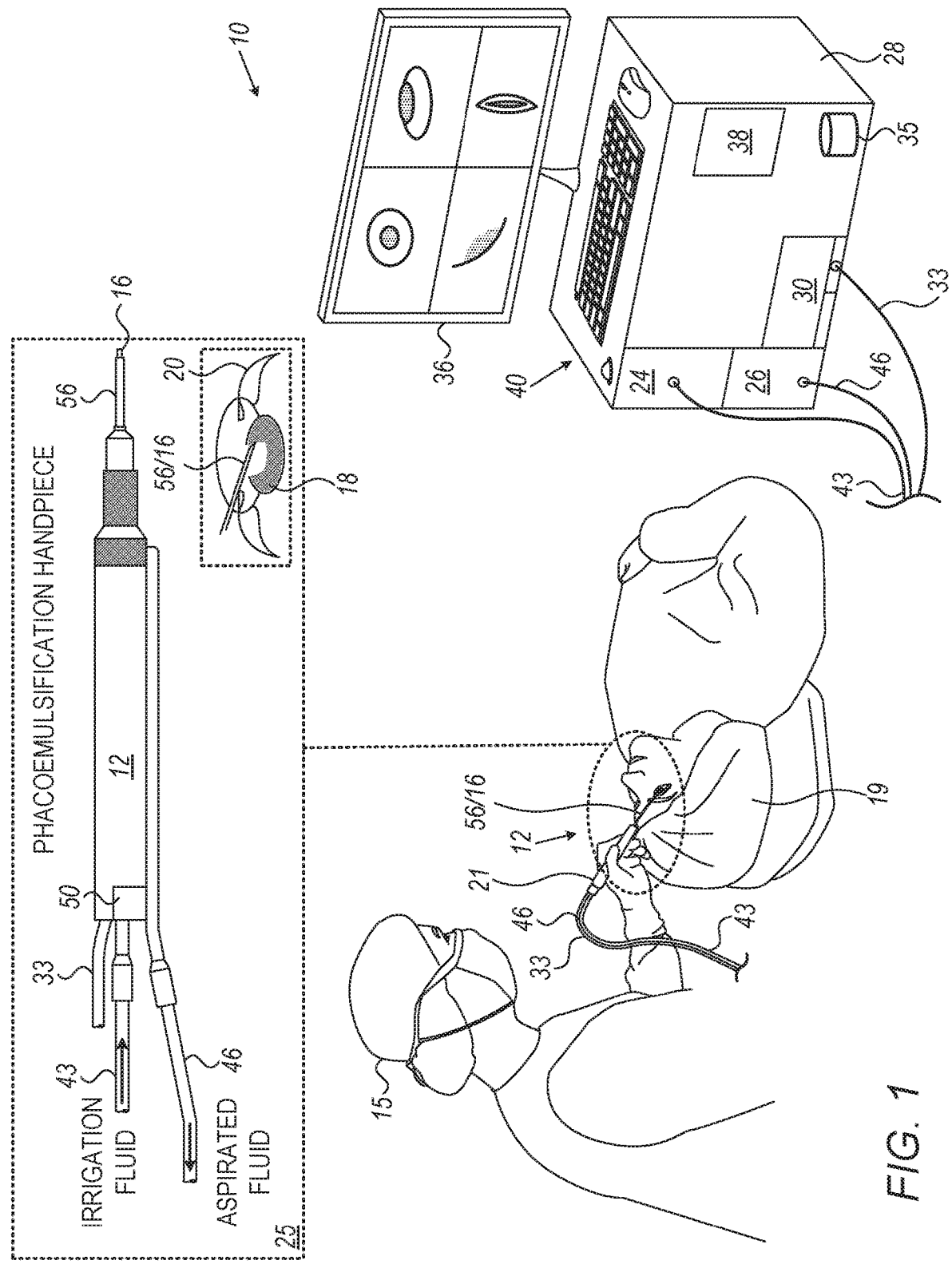
FIG. 1 is a schematic, pictorial view, along with an orthographic side view, of a phacoemulsification apparatus comprising a phacoemulsification probe comprising an aspiration bypass control (ABC), in accordance with an embodiment of the present invention.

During phacoemulsification of an eye lens, the emulsified lens particles are aspirated. When a particle blocks the inlet of the aspiration channel the vacuum in the line increases. When the line becomes unblocked (e.g., by the particle being subsequently sucked into the line), the high vacuum in the line causes an aspiration surge with potentially traumatic consequences to the eye.

A possible solution to the problem of vacuum level surge is incorporating an aspiration bypass. Such a bypass may consist of a small hole or channel between the irrigation channel and the aspiration channel. When a blockage occurs, the high vacuum diverts irrigation fluid into the aspiration channel via the hole, thereby limiting the vacuum level.

However, the above-described bypass aspiration technique is still prone to produce a traumatic aspiration surge when the line unblocks, since the high vacuum is present in a long line between a portion of the aspiration channel inside the emulsification probe and the aspiration pump, and that large, partially vacant volume, may therefore cause a surge. Moreover, diversion of irrigation fluid may cause an uncontrolled pressure fall in the irrigation channel, which may also pose a risk to the eye.

Embodiments of the present invention that are described hereinafter provide an aspiration bypass control (ABC) assembly to reduce risks from irregular performance of aspiration and/or irrigation. (e.g., to control the amount of direct flow of irrigation fluid from the irrigation channel to the aspiration channel, not via the eye), so as to control fluid pressure in the two channels. In some embodiments, the ABC assembly is located at a proximal part of the phacoemulsification probe and comprises a bypass channel for fluid communication between the irrigation and aspiration channels of the probe and a processor controlled valve that allows complete flow control in the aspiration line to maintain pressure and vacuum readings in the respective channels within prespecified limits.

Typically, the valve allows aspiration capacity that varies between a full flow of aspirated fluid with no irrigation fluid diversion into the aspiration channel and, in case of a blockage of the aspiration line, complete diversion of the irrigation fluid. Between these states, the valve is controlled (e.g., rotated) by the processor in an intermediate regime that maintains the pressures within desired ranges.

Moving the bypass channel from a fixed opening in the tip to a valve-controlled channel in the handle has considerable benefits in reducing the vacuum surge. Using a valve to simultaneously disconnect the eye from the vacuumed aspiration line and divert the irrigation into that line means that only vacuum in the short section of the aspiration line within the probe (between the valve and the eye) affects the eye. In contrast, when using an opening in the tip for bypass, the vacuum in the entire length of the aspiration line, all the way to the console, typically 5-6 ft long, affects the eye. As response time to a vacuum surge is largely proportional to the vacant volume, placing a valve in the handle reduces the response time considerably (e.g., from tens of mSec to a few mSec), and therefore reduces the risk of eye trauma.

In an embodiment, a rotatable valve is provided that can be rotated to open the bypass channel while at the same time close the aspiration channel. This combined action allows for a fast correction (e.g., on the order of several milliseconds) to a detected vacuum surge. Nevertheless, other valve types, such as linear valves, may be used instead of a rotatable valve. Whatever valve configuration is selected, the processor operates the valve to prevent reduced vacuum in the aspiration line to the pump, preventing an aspiration surge when the line unblocks.

The processor may be located in a console holding the aspiration pump, or in the handle of the phacoemulsification handpiece. By providing dynamic bypass aspiration control, the disclosed technique may improve the safety and efficacy of phacoemulsification procedures.

System Description

FIG. 1 is a schematic, pictorial view, along with an orthographic side view, of a phacoemulsification apparatus 10 comprising a phacoemulsification probe 12 comprising an aspiration bypass control (ABC) 50, in accordance with an embodiment of the present invention.

As seen in the pictorial view of phacoemulsification apparatus 10, and in inset 25, phacoemulsification probe (e.g., a handpiece 12) comprises a needle 16 and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, irrigation sleeve may have one or more side ports at or near the distal end to allow irrigation fluid to flow towards the distal end of the handpiece through the fluid pathway and out of the port(s).

Needle 16 is configured for insertion into a lens capsule 18 of an eye 20 of a patient 19 by a physician 15 to remove a cataract. While the needle (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, CA, USA.

In the shown embodiment, during the phacoemulsification procedure, a pumping sub-system 24 comprised in a console 28 pumps irrigation fluid from an irrigation reservoir to the irrigation sleeve 56 to irrigate the eye. The fluid is pumped via an irrigation tubing line 43 running from the console 28 to an irrigation channel 43a of probe 12. Eye fluid and waste matter (e.g., emulsified parts of the cataract) are aspirated via hollow needle 16 to the collection receptacle by a pumping sub-system 26, also comprised in console 28, using an aspiration tubing line 46 running from aspiration channel 46a of probe 12 to console 28. In another embodiment, the pumping sub-system 24 may be coupled or replaced with a gravity fed irrigation source such as a BSS bottle/bag.

Apparatus 10 includes a bypass aspiration control (ABC) system 50 to reduce risks to eye 20 from irregular performance of aspiration and/or irrigation, such as from a vacuum surge. To this end, the disclosed ABC system establishes variable fluid communication between aspiration channel 46a and irrigation channel 43a to control the flow of fluid between the two channels/tubing lines, so as to maintain pressures in the two channels/tubing lines within prespecified limits.

Phacoemulsification probe 12 includes other elements (not shown), such as a piezoelectric crystal coupled to a horn to drive vibration of needle 16. The piezoelectric crystal is configured to vibrate needle 16 in a resonant vibration mode. The vibration of needle 16 is used to break a cataract into small pieces during a phacoemulsification procedure. Console 28 comprises a piezoelectric drive module 30, coupled with the piezoelectric crystal, using electrical wiring running in a cable 33. Drive module 30 is controlled by a processor 38 and conveys processor-controlled driving signals via cable 33 to, for example, maintain needle 16 at maximal vibration amplitude. The drive module may be realized in hardware or software, for example, in a proportional-integral-derivative (PID) control architecture.

Processor 38 may receive user-based commands via a user interface 40, which may include setting a vibration mode and/or frequency of the piezoelectric crystal, and setting or adjusting an irrigation and/or aspiration rate of the pumping sub-systems 24/26. In an embodiment, user interface 40 and display 36 may be combined as a single touch screen graphical user interface. In an embodiment, the physician uses a foot pedal (not shown) as a means of control. Additionally, or alternatively, processor 38 may receive the user-based commands from controls located in a handle 21 of probe 12.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The apparatus shown in FIG. 1 may include further elements which are omitted for clarity of presentation. For example, physician 15 typically performs the procedure using a stereo-microscope or magnifying glasses, neither of which are shown. Physician 15 may use other surgical tools in addition to probe 12, which are also not shown in order to maintain clarity and simplicity of presentation.

Aspiration Bypass Control in a Phacoemulsification Probe

Figure 2A:
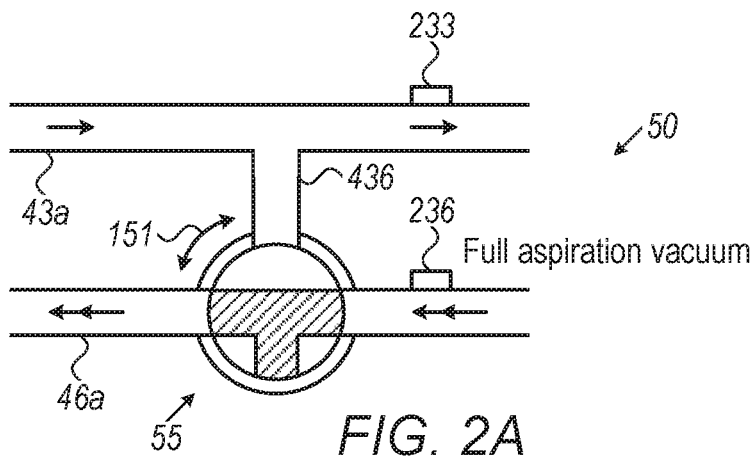
FIGS. 2A-2C are schematic, pictorial cross-sectional views of a rotatable valve of the aspiration bypass control (ABC) of FIG. 1 in different states of rotation, in accordance with an embodiment of the present invention.
Figure 2B:
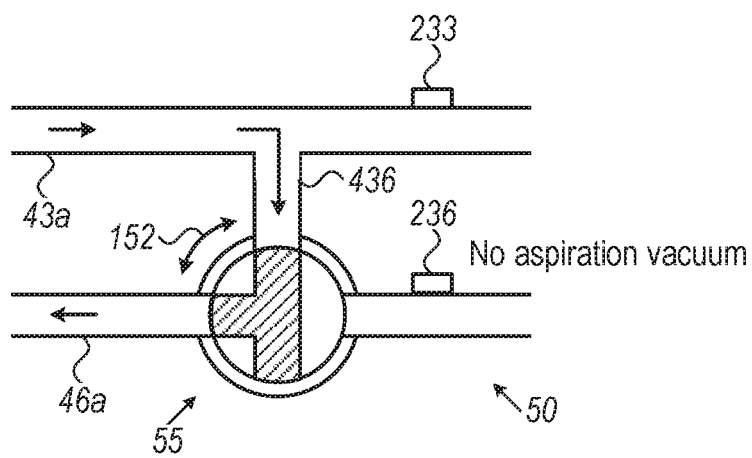
Figure 2C:
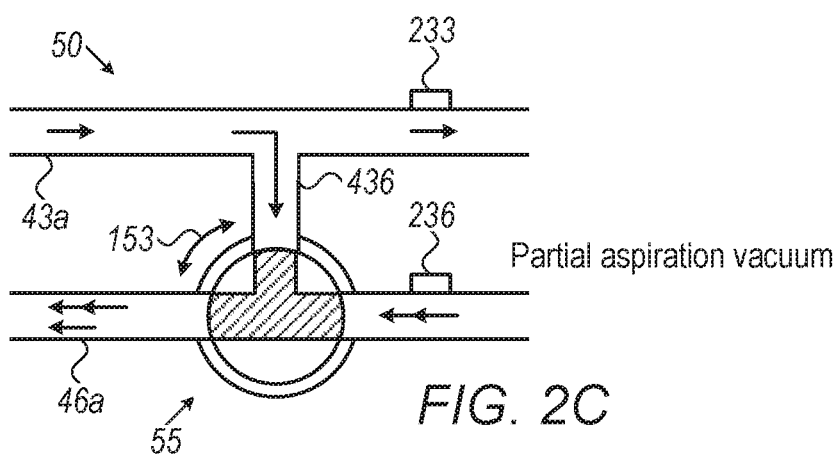

FIGS. 2A-2C are schematic, pictorial cross-sectional views of different states of rotatable valve 55 of aspiration bypass control (ABC) 50 of FIG. 1, in accordance with an embodiment of the present invention. As seen, valve selectively enables fluid communication between irrigation channel 43a and aspiration channel 46a via a bypass channel 436. Valve 55 is a motorized three-port rotatable valve typically including a motor driver and additional mechanical elements that are omitted for clarity of presentation.

A sensor 233, such as a pressure sensor or a flow sensor, measures the irrigation fluid pressure (or flow rate) in irrigation channel 43a distally to bypass channel 436, whereas a sensor 236, such as a pressure sensor or a vacuum sensor) measures the aspiration sub-pressure in aspiration channel 46a distally to bypass channel 436. The pressure/flow and pressure/vacuum measurements are performed close to the irrigation outlet and aspiration inlet, respectively, so as to provide an accurate indication of the actual pressures experienced by an eye and provide quick response time to a control loop.

The term "sensor" includes any types of sensors that can provide indication to the processor running the ABC assembly. For the aspiration channel, such sensor may be a pressure sensor that is configured to provide sufficiently accurate measurements of low sub-atmospheric pressures that are within a typical range of sub-pressures at which aspiration is applied (e.g., between 1 mm Hg and 650 mm Hg). In an embodiment, sensors 233 and 236 comprise the same pressure sensor model, with different settings/calibrations to measure either irrigation pressure or aspiration sub-pressure. For the irrigation channel, such sensor maybe the aforementioned pressure sensor, or a fluid flow rate meter.

In FIG. 2A, valve 55 is at a "full aspiration vacuum" angular orientation 151, at which there is a full flow of aspirated eye fluid (seen as leftward-facing double-headed arrows) proximally in aspiration channel 46a with no irrigation diversion from irrigation channel 43a into aspiration channel 46a. At the same time, there is a full flow of irrigation fluid (seen as rightward-facing single-headed arrows) distally.

In FIG. 2B, valve 55 is at a "no aspiration vacuum" angular orientation 152, at which the aspiration vacuum is fully disabled and bypass channel 436 is fully open to allow full irrigation diversion into aspiration channel 46a. The fully opened bypass channel reduces irrigation fluid to a minimum, which can be verified by pressure readings of sensor 233. The simultaneous action of the valve (to stop aspiration and divert irrigation fluid) gives the system a fast response time, needed, for example, to prevent trauma from a vacuum surge.

In FIG. 2C, valve 55 is at a "partial aspiration vacuum" angular orientation 153, at which there is a full flow of aspirated fluid but also full irrigation diversion from the irrigation channel 43a into aspiration channel 46a. The fully opened bypass channel causes some irrigation fluid to be diverted and combine with eye fluids aspirated proximally, thereby reducing irrigation pressure to a prespecified value, or within a range of values, as verified by pressure sensor 233. The intermediate, partial aspiration vacuum can be adjusted by rotating valve 55 about the position shown in FIG. 2C, and/or by processor controlling the irrigation output flow, and/or by processor 38 controlling aspiration suction power of subsystems 24 and 26, respectively.

Figure 3A:
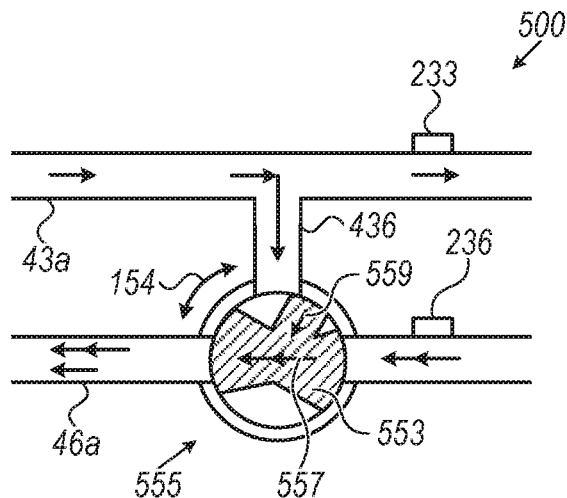
FIGS. 3A and 3B are schematic, pictorial cross-sectional views of a rotatable valve of an aspiration bypass control (ABC), in accordance with another embodiment of the present invention.
Figure 3B:
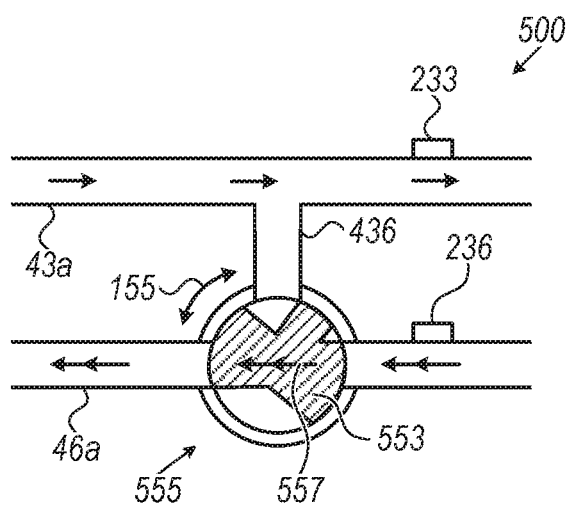

FIGS. 3A and 3B are schematic, pictorial cross-sectional views of a rotatable valve 555 of an aspiration bypass control (ABC) 500, in accordance with another embodiment of the present invention. ABC 500 can be used in place of ABC 50 in the system of FIG. 1, and be similarly controlled by processor 38 in response to readings from sensors such as sensors 233 and 236 to perform the actions of ABC 50 shown in FIGS. 2A-2C (e.g., by being rotated into same orientations 151, 152, 153). In contrast to the embodiment of FIGS. 2A-2C, however, in the present embodiment the valve has a continuous range of orientations (e.g., 154, 155) that provides a continuous control over the extent of fluid communication between the irrigation channel and the aspiration channel, while at a same time maintaining aspiration channel 46a fully open.

As seen in FIG. 3A, valve 555 is at an angular orientation 154 that allows only a small flow 559 of irrigation fluid via bypass channel 436 into aspiration channel 46a. As further seen, a passage 553 for aspiration of valve 555 is shaped with an angular sectional opening that maintains full flow of aspiration (557) for a wide range of bypass openings, from full opening of channel 436, such as used in the view of FIG. 2c, to no opening (e.g., valve 555 rotated clockwise at 45°, as shown in FIG. 3B, from a full bypass opening orientation). This design may be useful by allowing the regulation of aspiration solely via a variable opening bypass line, which may be preferred by some clinicians in order to avoid abrupt changes in the aspiration/irrigation channels initiated by the control system. The above valve design is brought by way of example, and other possible designs of the rotatable valve, which may occur to a person skilled in the art, are covered by this invention.

Figure 4:
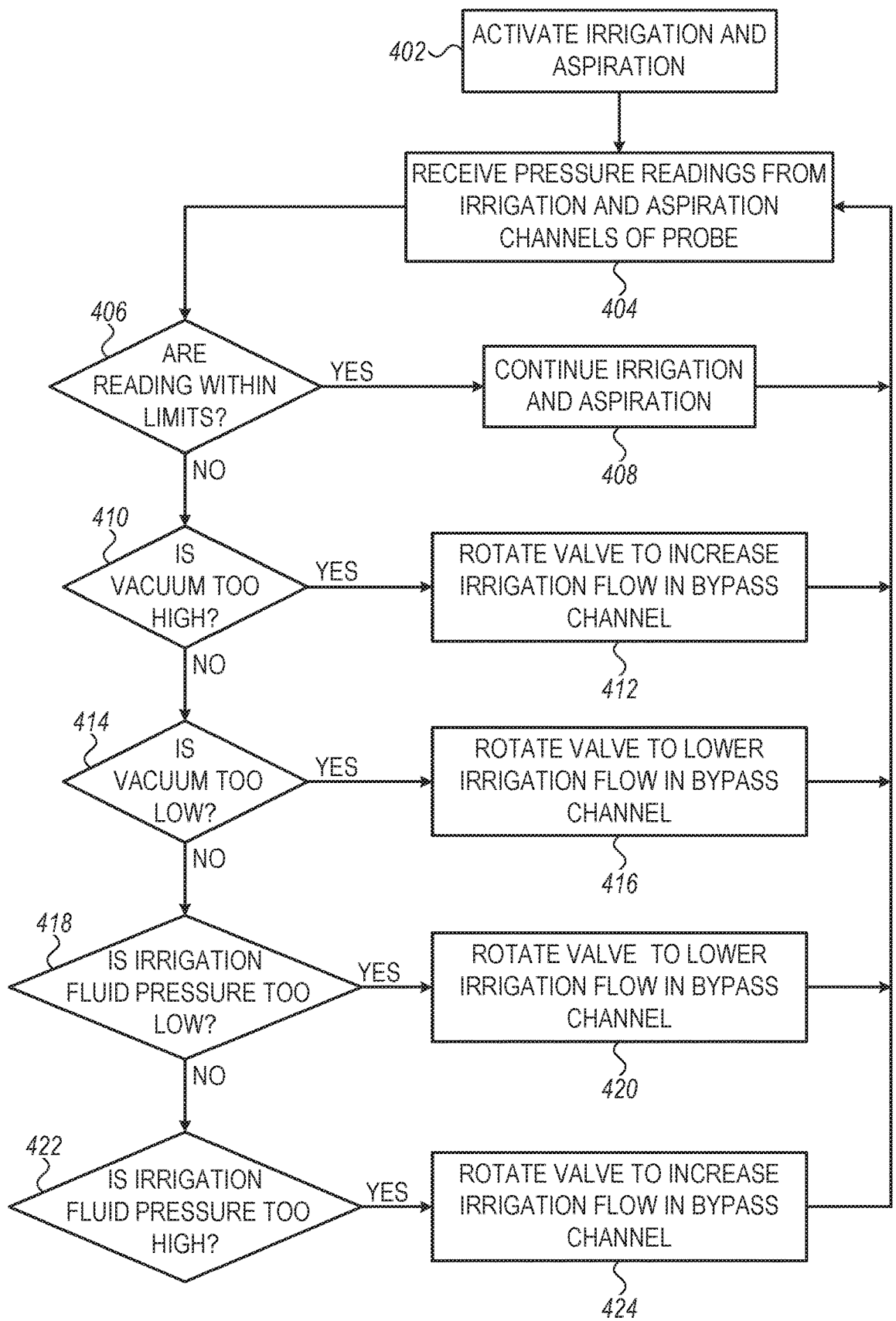
FIG. 4 is a flow chart schematically illustrating a method for controlling aspiration and irrigation of the phacoemulsification probe of FIG. 1 using its aspiration bypass control (ABC), in accordance with an embodiment of the present invention.

FIG. 4 is a flow chart schematically illustrating a method for controlling aspiration and irrigation of phacoemulsification probe 12 of FIG. 1 using its aspiration bypass control (ABC) 50, in accordance with an embodiment of the present invention. The algorithm, according to the presented embodiment, carries out a process that begins after physician 15 inserts phacoemulsification needle 16 of probe 12 into a lens capsule 18 of an eye 20.

At a phacoemulsification starting step 402, physician 15 vibrates needle 16 to break a cataract and, at the same time, processor 38 activates the aforementioned irrigation and aspiration functions of the probe.

Next, processor 38 receives pressure readings from irrigation and aspiration channels 43a and 46a, acquired by pressure and vacuum sensors 233 and 236 respectively, at a pressure reading receiving step 404.

At pressure checking step 406, processor 38 checks if the readings fall within prespecified limits. If they do, processor 38 continues applying the same irrigation and aspiration rate (408) and the process returns to reading step 404.

In steps 412, 416, 420 and 424 below, the three-way rotatable valve is configured to simultaneously adjust an opening of the bypass channel while inversely adjusting the opening of the aspiration channel.

If the readings do not fall within prespecified limits, processor 38 checks if the vacuum reading is too high (e.g., if a risk of vacuum surge has been realized), at vacuum level checking step 410. If the vacuum reading is too high processor 38 sends a signal causing valve 55 to rotate to increase (412) an opening in the bypass channel 436 so as to increase irrigation fluid flow into aspiration channel 46a, and the process returns to reading step 404.

The entire checking cycle and application of a corrective action described above, and any of these entire cycles described below, typically take no more than few milliseconds, thereby ensuring that no damage is caused to the eye from irrigation and/or aspiration problems.

If the vacuum reading, as found in vacuum level checking step 414 is too low (i.e., vacuum is insufficient), processor 38 sends a signal causing valve 55 to rotate to decrease (416) an opening in the bypass channel 436 so as to decrease irrigation fluid flow into aspiration channel 46a, and the process returns to reading step 404.

If the irrigation fluid pressure reading, as found in irrigation pressure level checking step 418, is too low (e.g., irrigation fluid flow is insufficient), processor 38 rotates valve 55 to decrease (420) an opening in the bypass channel 436 so as to increase irrigation fluid flow distally in channel 43 due to a decreased irrigation fluid flow into aspiration channel 46a, and the process returns to reading step 404.

If the irrigation fluid pressure reading, as found in irrigation pressure level checking step 422, is too high (e.g., irrigation fluid flow is not compensated well enough by aspiration), processor 38 rotates valve 55 to increase (424) an opening in the bypass channel 436 so as to decrease irrigation fluid flow distally in channel 43 due to the increased irrigation fluid flow into aspiration channel 46a, and the process returns to reading step 404.

The example flow chart shown in FIG. 4 is chosen purely for the sake of conceptual clarity. For example, additional steps, such controlling pumping systems 24 and 26, are omitted for simplicity and clarity of presentation. Furthermore, various irrigation/aspiration termination criteria, for example, when a predefined number of control cycles fails to bring pressures within limits, or when such a failure is due to other problems, are omitted for simplicity of presentation.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A phacoemulsification system, comprising:
a phacoemulsification probe, comprising:
a needle, which is configured to be inserted into a lens capsule of an eye and to be vibrated to emulsify a lens of the eye;
an irrigation channel for flowing irrigation fluid into the lens capsule;
an aspiration channel for removing material from the lens capsule;
a bypass channel fluidly coupled with the irrigation channel and with the aspiration channel;
a single processor-controlled valve configured to control a level of fluid communication between the irrigation channel and the aspiration channel via the bypass channel; and
one or more sensors configured to measure fluid pressure at a distal portion of one or both of the irrigation channel and the aspiration channel;
a processor, which is configured to adaptively adjust the valve based on the fluid pressure measured by the one or more sensors; and
wherein, in a first position, the single processor-controlled valve blocks a flow of aspiration from the needle to the aspiration channel and diverts a flow of irrigation fluid into the aspiration channel via the bypass channel.

2. The phacoemulsification system according to claim 1, wherein the processor is configured to adjust the valve so as to maintain a vacuum level in the aspiration channel within a pre-specified limit.

3. The phacoemulsification system according to claim 1, wherein the processor is configured to adjust the valve so as to maintain a pressure level in the irrigation channel within a pre-specified limit.

4. The phacoemulsification system according to claim 1, wherein the one or more sensors comprise (i) a pressure sensor coupled to the distal portion of the irrigation channel, and (ii) a vacuum sensor coupled to the distal portion of the aspiration channel.

5. The phacoemulsification system according to claim 1, wherein the processor is configured to adjust the level of fluid communication by adjusting, using the valve, an opening of the bypass channel between the irrigation channel and the aspiration channel.

6. The phacoemulsification system according to claim 1, wherein the valve is a three-way rotatable valve.

7. The phacoemulsification system according to claim 6, wherein the three-way rotatable valve is configured to simultaneously adjust an opening of the bypass channel while inversely adjusting the opening of the aspiration channel.

8. The phacoemulsification system according to claim 1, wherein the processor is comprised in the probe.

9. A method, comprising:
inserting into an eye a phacoemulsification probe comprising a needle, an irrigation channel, an aspiration channel, a bypass channel, and a single processor-controlled valve, wherein the bypass channel fluidly couples the irrigation channel to the aspiration channel, wherein the valve is coupled with the bypass channel and the aspiration channel and is configured to control a level of fluid communication between the irrigation channel and the aspiration channel; and wherein, in a first position, the single processor-controlled valve blocks a flow of aspiration from the needle to the aspiration channel and diverts a flow of irrigation fluid into the aspiration channel via the bypass channel;
vibrating the needle to emulsify a lens of the eye;
flowing irrigation fluid via the irrigation channel into a lens capsule of the eye;
removing material from the lens capsule via the aspiration channel; and
using a processor,
measuring fluid pressure at a distal portion of one or both of the irrigation channel and the aspiration channel, and adaptively adjusting the valve based on the measured fluid pressure.

10. The method according to claim 9, wherein adaptively adjusting the valve comprises adjusting the valve so as to maintain a vacuum level in the aspiration channel within a pre-specified limit.

11. The method according to claim 9, wherein adaptively adjusting the valve comprises adjusting the valve so as to maintain a pressure level in the irrigation channel within a pre-specified limit.

12. The method according to claim 9, wherein adaptively adjusting the valve comprises adjusting, using the valve, an opening of the bypass channel between the irrigation channel and the aspiration channel.

13. The method according to claim 12, wherein adaptively adjusting the valve comprises simultaneously adjusting the opening of the bypass channel while inversely adjusting the opening of the aspiration channel.

* * * * *